United States Patent

Crites

[11] Patent Number: 4,484,132
[45] Date of Patent: Nov. 20, 1984

[54] CRACK DETECTING SYSTEM

[76] Inventor: Nelson A. Crites, 3 Gateway Estates, Florida City, Fla. 33034

[21] Appl. No.: 241,507

[22] Filed: Mar. 9, 1981

[51] Int. Cl.³ ................. G01R 31/02; G01R 31/12
[52] U.S. Cl. ................................ 324/54; 73/776
[58] Field of Search .............. 73/768, 776, 775; 324/65 R, 51, 54; 338/223; 29/593, 620

[56] References Cited

U.S. PATENT DOCUMENTS

| | | | |
|---|---|---|---|
| 3,603,142 | 9/1971 | Saylak | 73/776 |
| 3,721,898 | 3/1973 | Dragoumis | |
| 3,803,485 | 4/1974 | Crites | 324/65 R |
| 4,255,974 | 3/1981 | Dufrane | 73/776 |

FOREIGN PATENT DOCUMENTS 141175  11/1979  Japan ................................ 324/51

Primary Examiner—Stanley T. Krawczewicz
Assistant Examiner—Jose M. Solis
Attorney, Agent, or Firm—William V. Miller

[57] ABSTRACT

A crack or rupture-detecting system comprising an electrically-insulating substrate which carries lines of electrically-conducting material formed of small electrically conductive particles which are in electrical contact. The substrate layer may be elastomeric when applied to the object to be protected, but later will crack or rupture if a crack or rupture occurs in the object and layer and thereby separate the particles in the conducting line or lines adjacent the crack or rupture.

12 Claims, 11 Drawing Figures

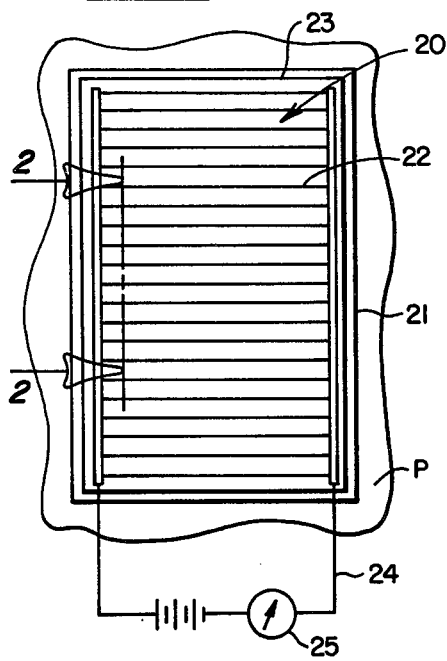
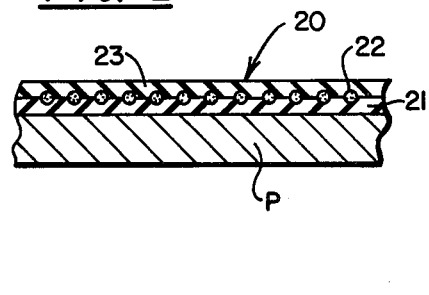
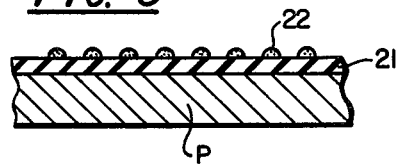
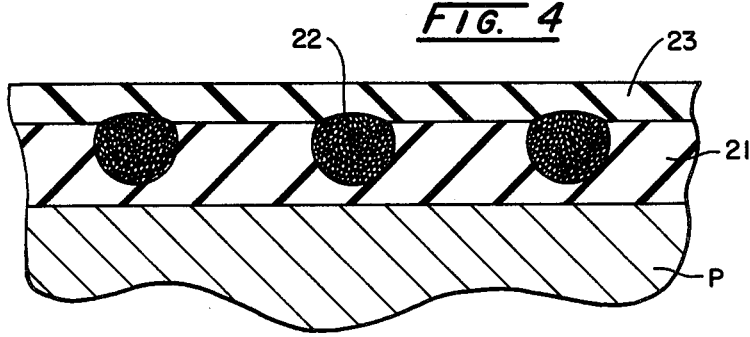
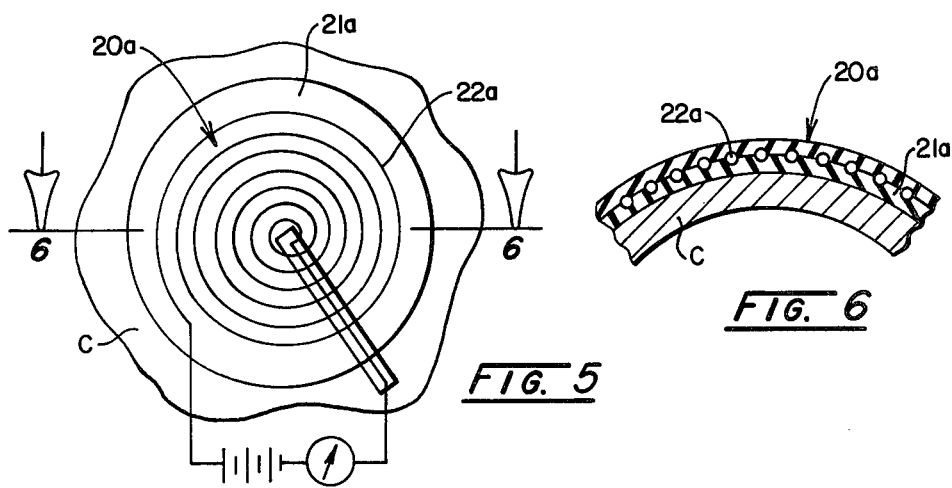

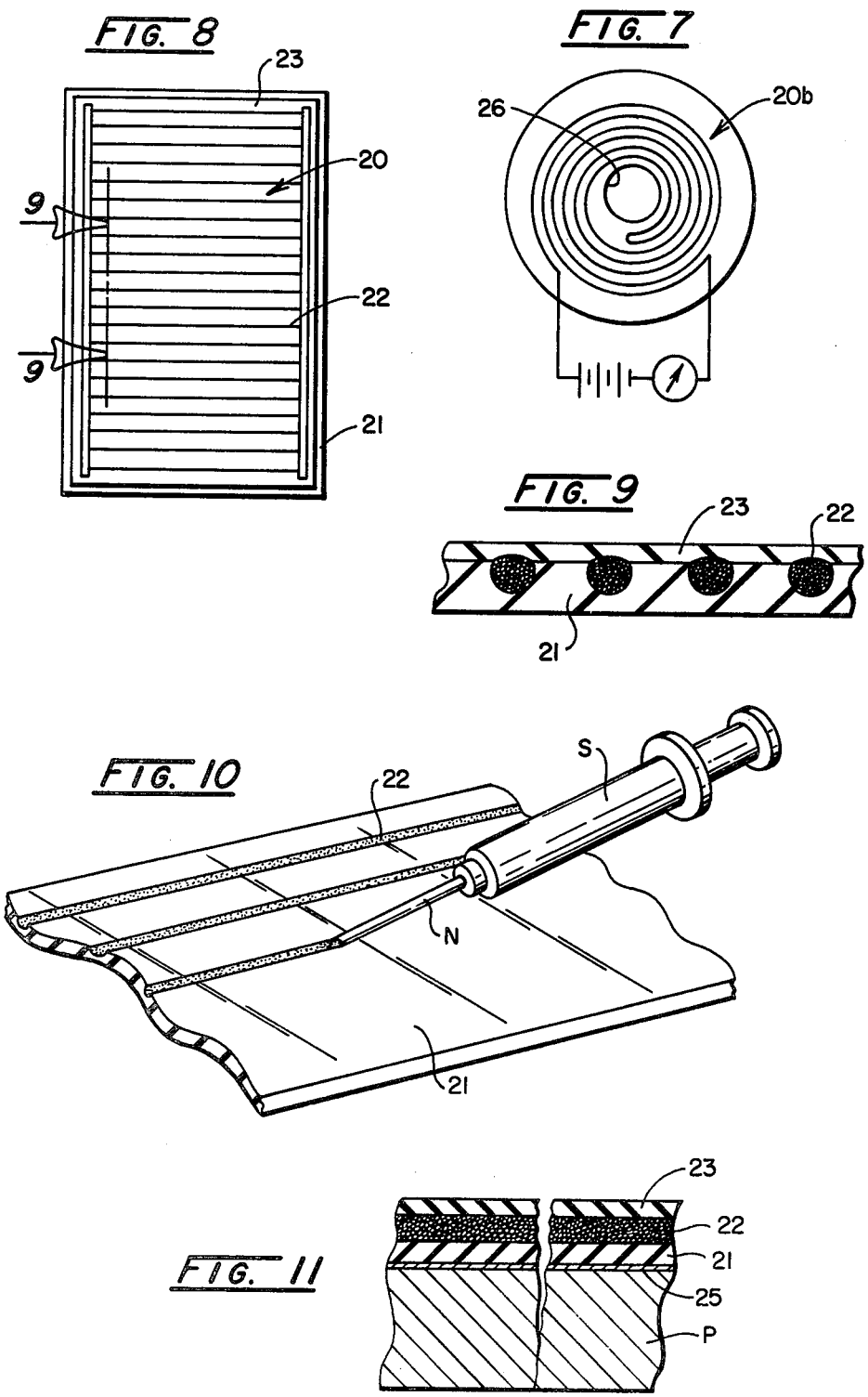

CRACK DETECTING SYSTEM

BACKGROUND AND PRIOR ART

It is very desirable in many instances to detect cracking or rupturing in various structures to avoid damage to the structures and even loss of life or limb due to failure of such structures. Many different systems have been devised to monitor and detect cracks or other defects in structures to which they are applied.

Prior art systems have included indicating devices consisting of electrical conductors in the form of wires or thin metallic ribbons of conducting metals bonded to an insulating substrate. The substrate with the bonded conductors may be wrapped around or cemented flat to areas that may rupture from strain or stress. An example of such a system is disclosed in the patent to Dragoumis, U.S. Pat. No. 3,721,898. However, in these crack or rupture-indicating systems the rupture-sensing solid metal conductors themselves can crack either from fatigue or stress even before the monitored structure itself, to which the substrate is applied. If the solid conductors are made of ductile metals, so that they are not too brittle as to break under small elongations, they will usually then have low fatugue life, but even worse, will stretch and span the crack. The reverse is also generally true since high strength of the solid metal rupture-sensing conductors usually means low elongation thereof under stress which will render the rupture-sensing conductors unable to withstand elongations normally expected of the structures to which the substrate is applied. Even though some suitable combinations can be found for some applications, this type of solid metal rupture-sensing conductor bonded to a substrate cannot be used in many applications where the monitored structures have complex uneven surfaces sometimes having multiple curvatures.

Another prior art approach to the crack-detecting problem is illustrated in the patent to Crites U.S. Pat. No. 3,803,485. This patent discloses a system which uses microencapsulated conducting liquids embedded in a coating that can be applied to the surface of the structure to be protected, and can be hardened in place, with a top covering layer of conducting material. This system works very successfully in some applications but is difficult to apply to the structure without rupturing one or more of the capsules. Also, if too much pressure is applied to the coating or the coating is struck with a sufficient blow, a rupture of capsules will take place, indicating falsely that a crack or rupture has occurred in the structure being monitored. Moreover, at extremely low temperatures, the conducting liquids in the capsules do not really flow so as to allow the system to function as intended.

Other prior art rupture-detecting systems involve the use of special metallic grids that are usually photo-etched on a substrate to be applied to the structure to be monitored but these are usually quite expensive. Etched metal film, metal foil and electrically or vapor-deposited metal lines have been used but are difficult and expensive to use. These materials can also fatigue along with the structures to which they are applied, or even before, giving incorrect warning information.

The rupture-detecting system disclosed herein overcomes all of the problems of the above-mentioned prior art systems and others and even accomplishes this with a great reduction in cost of manufacture and with ease of application in an effective manner.

SUMMARY OF THE INVENTION

The system of this invention comprises a substrate in the form of a sheet or layer of electrically-insulating material, preferably elastomeric, which is applied to the surface to be monitored and which will become brittle naturally or will be treated to make it brittle. Upon this substrate, is applied a pattern of conductor lines as a viscous substance consisting of conductive particles carried by sufficient liquid to make it flowable and which after evaporation leaves the conductive particles in continuous overlapping or contacting relationship to form an electrical path which will be broken upon cracking or rupturing of the underlying surface.

More specifically, according to this invention, the defect-detecting system comprises an electrically-insulating substrate base or layer which is applied in intimate contact to the surface of a metallic or non-metallic structure to be protected. This layer will carry conductor lines, in a selected geometric pattern, of particulate electrical conducting material, the particles being in electrical contact with each other. The substrate base will preferably be in the form of a thin sheet or tape of elastomeric material which can be quite pliable when applied to the structural surface and will adhere thereto but which will become hardened, after application, so that it will crack or rupture if the metal under it were to crack or rupture. For flat or singly curved surfaces, the sheet or tape needs only to be flexible; however, for general use, where surfaces are doubly curved or irregular, the pliable material will be needed so it will have sufficient plasticity to retain the shape into which it is formed. Upon this sheet or tape, usually prior to application, an electrically-conductive line or lines of particulate material is imprinted or formed in a suitable geometric pattern, such as grids, concentric circles, ellipses, or other appropriate electrically-conducting patterns, that will be broken if the surface to which the substrate is applied develops a crack or rupture. The particulate conducting material, which forms the conducting lines, may be applied as a viscous flowable semi-liquid substance, similar to an ink or a glue, which is compatible with the substrate so that it will adhere thereto and will not shatter or crack unless the substrate sheet or tape cracks. Also, the conductive substance will not degrade and lose its conductivity as the result of passage of time or because of environmental conditions. Multiple layers of the substrate may be used on the surface with the conducting lines of the suitable geometric patterns, crossing, so that cracks in the surface that might grow in diverse directions, would crack one or more of the layers and thus break the conducting lines thereon. The system will also include electrical leads connected to the electrically-conducting lines on the substrate and to electrically-indicating devices. These devices would indicate if a crack or separation had occurred in the electrically-conducting lines mounted on the thin substrate and thus in the underlying structure. The cracks or breaks in the substrate would interrupt the electrical continuity of the particulate substance, imprinted or formed thereon, by separating the particles at the crack.

It will be understood that the conductive lines of the system of this invention are formed by the small conductive particles which overlap and contact with each other to produce the continuous conductive lines. Thus, the lines are conductive and flexible and will not fatigue themselves, but will only separate when fatigue actually occurs in the surface which carries the substrate, to cause separation of the conductive lines.

BRIEF DESCRIPTION OF THE DRAWINGS

The best mode contemplated in carrying out this invention is illustrated in the accompanying drawings in which:

FIG. 1 is a plan view showing a plane metal surface with the crack-detecting system of this invention applied thereto with the conducting lines on the substrate in the form of a grid;

FIG. 2 is a sectional view taken on line 2—2 of FIG. 1;

FIG. 3 is a view similar to FIG. 2 but showing a form of the invention in which the outer protective layer is eliminated;

FIG. 4 is an enlarged portion of the sectional view of FIG. 2;

FIG. 5 is another example of the invention with the system applied to a curved surface and with the conducting lines applied to the substrate in a spiral pattern;

FIG. 6 is an enlarged sectional view taken along line 6—6 of FIG. 5;

FIG. 7 shows a modification of the FIG. 5 arrangement;

FIG. 8 shows the substrate with conducting lines, of the type used in FIG. 1, before it is applied to the metal structure;

FIG. 9 is an enlarged sectional view taken along line 9—9 of FIG. 8;

FIG. 10 is a schematic view showing one method of applying the conductive lines to the substrate base; and FIG. 11 is a schematic sectional view showing how the particles on the substrate separate when a crack in the metal and overlying substrate occurs.

DETAILED DESCRIPTION OF THE INVENTION

As pointed out previously, the crack or rupture-detecting system of this invention may be applied to plane, singly curved, doubly curved or irregular surfaces of various structures to be monitored and protected. The system comprises basically a electrically-insulating substrate or base layer which carries lines of particulate conductive material with the particles thereof overlapping and in electrical contact. The base layer or substrate is preferably inherently flexible or can be made pliable or plastic before application to the structural surface by a suitable solvent or softener. It will subsequently harden or set, or be treated to do so, so that cracking or rupturing of the underlying surface will produce cracking or rupturing thereof as well as cracking or separation of the lines carried thereby as a result of separation of the conductive particles adjacent the crack. The conductive particles are applied in the form of a flowable viscous substance consisting of a liquid carrier and the conductive particles of a suitable size. The liquid carrier will be compatible with the substrate or base material and, as it dries or sets, will adhere to or combine with the substrate material, leaving a deposit of the overlapping and contacting conductive particles to form the conducting lines thereon.

The substrate layer or base can be a thin pliable sheet or tape, preferably of a suitable plastic. It can be partially cured, then cooled to interrupt the hardening, so that it can be pliable when warmed and can be applied to the structural surface and subsequently completely cured and hardened. It also can be a thin sheet of plastic, or even thin paper, that might be softened so that it can be shaped or formed to the geometry of the metal structure. For example, a cellulose acetate sheet can be softened with a solvent, then formed and bonded to the surface of the structure.

The conducting lines can be of various materials in particle form with the particles ranging in size from 1 to 100 microns. For example, particles of electrically conducting carbon (graphite), silver, gold, platinum or even finely particulate alloy materials and many other conductive materials can be used. The particles will preferably be mixed with a suitable liquid carrier until a flowable viscous substance is formed which will be similar to an ink or glue. The particles are preferably used in varying amounts, for example:

from 15 to 100 parts by weight of conducting graphite to 100 parts of liquid carrier;

or 2 to 3 parts of metal particles to 1 of liquid carrier.

The flowable substance with the conducting particles may be applied in various ways as with a syringe or pen which creates patterns on the substrate as it flows the substance thereon to form the conducting lines, the liquid of the flowable substance then drying or setting to combine with the material of the substrate under controlled conditions and evaporating to leave the contacting or overlapping particles in electrical contact. The flowable substance with the conducting particles may be applied in various other ways such as by etching channels in the substrate and flowing the substance into those channels which will subsequently set or harden to form deposits of the conducting particles, embossing or printing lines of the flowable substance on the substrate, etc. In each case, the liquid carrier will be compatible with the base layer and will either combine with or adhere thereto as it dries or sets.

The drawings illustrate examples of the application of this system but many other applications are possible.

In FIGS. 1 and 2, there is shown a crack-detecting system, indicated generally by the numeral 20, applied to a plane surface P of a metal structure to be monitored and protected. The system 20 comprises the electrically-insulating substrate or base layer 21 which carries the electrically-conducting lines 22 arranged in a suitable geometric pattern, a grid-like pattern being illustrated. The conductive lines 22 are covered by an electrically-insulating layer 23 which is applied to the upper surface of the substrate 21. This insulating layer is compatible with and adheres to the substrate layer. Electrical leads 24 are connected to the grid and are connected to an indicating instrument 25 which will indicate when any of the conductive lines 22 are broken by rupturing or cracking of the metal surface P which produces cracking of the substrate layer 21 and the conductive lines 22 carried thereby. The manner in which this occurs is indicated schematically in FIG. 11. The nature of these conducting lines is indicated in the enlarged section of FIG. 9. This shows that the small particles overlap and contact normally so that the resulting lines will be electrically conductive but that they can be separated so that the lines will be non-conductive, as shown in FIG. 11, and as a result of the layer 21 cracking. The conductive lines may be recessed in the substrate 21 as shown in FIGS. 2 and 4 or may be merely embossed thereon as shown in FIG. 3. Also, as indicated in FIG. 11, a cement coating 25 may be used in securing substrate 21 to the surface of the structure P. This coating of cement must be compatible with the substrate layer and preferably is of the same material.

In FIG. 5 and 6 the system 20a is shown applied to a curved surface C of a metal structure to be monitored. In this case, the conductive lines 22a are shown arranged in a spiral pattern. The curved surface C includes a convex curve and when the substrate layer 21a is applied thereto it will be sufficiently flexible that it may be made to conform this curve.

FIG. 7 shows a spiral arrangement 20b similar to that shown in FIG. 5 except it is flat and has a central opening 26 through which a bolt could pass. Thus, this arrangement could be used in monitoring the head of a bolt.

As indicated in FIGS. 8, 9 and 10, the substrate layer 21 is preferably formed before application to the structure to be protected and monitored for cracks or other defects. Also, the conducting lines 22 are applied thereto in a suitable manner and are covered with the insulating layer 23.

One way in which the conducting lines 22 can be formed is illustrated in FIG. 10. The flowable substance, consisting of the liquid carrier and conducting particles in suitable size and quantity, may be provided in a syringe S of a suitable type. The needle N thereof is engaged with an pulled along the surface of the layer 21 to form a groove therein and simultaneously flow the substance into the groove. The filled groove will appear as in FIG. 9. In this manner a conductive line 22 is formed. Many other methods may be used for forming the conductive pattern. Then the non-conducting layer 21, with the conducting lines 22 thereon, may be covered with the non-conducting layer 23 (FIG. 2) and the unit is now ready to apply to the metal surface to be monitored. For some applications the layer 23 is not necessary (FIG. 3). It may be desirable to use a coating of cement between the substrate and underlying surface as shown in FIG. 11.

The main requirements of the system is that it employ a base or substrate, preferably elastomeric to be applied to the surface to be monitored and that the base will have formed thereon the conductive lines produced by the small conductive particles which will under normal conditions electrically contact with each other. The final requirement is that the substrate or base material is hardened or will harden, after application to the surface or forming thereon, so that, if the stressed member should develop a crack at the surface, the applied protecting layer of material will also crack.

As the substrate material, elastomeric sheet materials will be most useful for this invention, i.e., if they are electrically insulating and are or can be made brittle. By being brittle, is meant that they will crack or rupture, if subjected to elongations in excess of 20 percent throughout the working temperature range of the structure to which they are applied. This means that they should never rupture under 7 to 8 percent but should always rupture if subjected to over 20 percent elongation. This would not exclude fibrous sheet materials or filled fibrous materials if they will crack as described above. Many of the applications will be on plane flat surfaces or singly curved surfaces. For these applications the material need only be flexible not pliable or plastic. If the surface is doubly curved or irregular, the material will need to be pliable or stretchable non elastically, i.e., so that if deformed it will stay deformed. When applying either the flexible or pliable material, it may be necessary to use a bonding cement that also will stay brittle along with the substrate. Upon a rise in temperature of the structure, in its normal working range, the bonding cement must not soften nor should the substrate sheet soften. The material that is pliable must have the capability of being hardened or embrittled after it is applied to the structure. In some materials, such as partially cured epoxies, where they were applied to doubly curved or irregular surfaces, they may be hardened in place, then removed and cemented to the surface. The substrate materials should be in the range of 0.00025 to 0.10 inches in thickness. The usual working range will be between 0.0002 to 0.005 inch. Where a top insulating protective coating is used, it may have, in addition, a metallic film as mechanical protection. If commercial sheet stock is used for the substrate, it may in some instances be necessary to bake the sheet material to further harden or embrittle the material. Examples of suitable sheet materials ae cellulose acetate or cellulose butyrate. These materials may be softened by soaking in a water-acetone solution. If polystyrene or methyl or ethyl acrylics are used, well known softeners can be used. If epoxyies are used, there is no solvent and the material will have to be used in the thin sheet form for conditions that require flexibility only, or the sheet may be only partially cured and then cooled to prevent further hardening until used. Then upon warming up, the sheet will become temporarily pliable until cross-linking hardens the sheet.

The hardenable viscous fluid, that is made conductive by adding sufficient electrically conductive fine particulate material to allow an electrical path to develop from continuous contact and overlapping of the particles, will have to be compatible with and bond to the substrate. In a preferred example, the fluid was commercial cellulose acetate cement with some plasticizer as an additive. In practice, sufficient super conducting carbon, such as Cabbott's Carbon LX-150, was added until electrical conduction was attained upon hardening. Conduction is improved upon hardening because the solvent is released, causing shrinking, thus compressing the microscopic fibers in the conducting carbon in contact with each other. Then to cause embrittling of the hardened conducting lines on the substrate, the material was baked to cause embrittling to take place. This was probably caused by vaporizing out the plasticizer. Varying amounts of super conducting carbon can be used, depending upon the ratio of the dry plastic dissolved in the solvent to make the viscous fluid. Super conducting carbon cannot be described by the usual particle size procedures since it is fibrous in nature but sizes of 10 to 15 microns are suitable. Since carbon has a much lower density than metals, the ratio of conducting carbon in parts by weight can be different from the metals. However, the fibrous nature of the carbon can achieve some conduction at comparatively low levels or ratios. A ratio of one part of superconducting carbon to one part of fluid usually produces a conducting line upon hardening. This ratio can be varied, 20% to 100% carbon to cellulose acetate by weight has been found suitable. However, conduction usually does not occur below 0.15 parts of carbon and one part of viscous fluid. If metallic particles such as copper or silver are used, the particles usually do not exceed the range of 5 to 100 microns. One mixture of copper powder and fluid, that produced good conduction upon hardening, contained two parts of copper to one of fluid by weight. A ratio of three to one produced excellent conduction. Excess of the metallic powder resulted in loss of fluidity and a tendency toward crumbling. If it is desired to make up the viscous fluid binder, one way it may be made is by adding one part by weight of the cellulose acetate to two parts of amyl acetate. Other solvents or their mixtures can be used depending upon the solubility of the cellulose acetate and the temperatures involved.

In addition to the electrical signal, as described above, indicating that a crack had occurred, it would be possible to locate the crack by means of other well-known crack-detecting procedures. For example, an electrostatic procedure using powder. In most cases, according to this invention, a protective insulating layer 23 or sheet would be applied over the substrate 21 having the conducting lines 22 thereon. A crack occurring in the metal structure, which resulted in cracking the substrate and protective layers, would produce a short to ground through the crack. The electrostatic powder would then deposit on the crack and would outline it. Another means of detecting the crack would be to apply an over-voltage to the conducting lines 22. The result would be the burning or discoloration of the cracked spot caused by the arcing.

Several examples of suitable detecting assemblies are described below:

EXAMPLE 1

A preferred application of this invention makes use of a finely divided super conducting graphite powder intimately mixed into a cellulose acetate base in which the cellulose acetate is dissolved in a suitable solvent or mixture of solvents such as for example, acetone or acetone and one of a number of petroleum base solvents. The conducting graphite powder is added until the conductivity (when the solvents, have been released) reaches a suitable level. This conducting glue-like ink is then traced on thin sheets of cellulose acetate in the geometric pattern desired and allowed to dry or harden. In this state, the sheet of cellulose acetate with, the conducting lines imprinted or traced thereon, is bonded to the flat or contoured surface that is subject to rupture or cracking. The cellulose acetate must be embrittled by baking if it will not crack at or beyond 20% elongation. Then, after electrically connecting the conducting lines in the desired manner, and providing an electric circuit for indicating changes of resistance, a crack or rupture-sensing coating will be availale that is not sensitive to fatigue; since the conducting particles are already in tiny but contacting pieces, it cannot fatigue. Also, since the hardened particle binder and substrate sheet are both of plastic (plastic is of low modulus), the assembly will not be as nearly as sensitive to fatigue as the metal base or other structure to which it is attached. However, the cellulose-acetate hardened substance containing the conducting graphite, along with the cellulose acetate base or substrate, can be softened by dipping the sheet, carrying the lines, in an acetone water solution or mixture. This unique feature allows the sheet with the conducting lines to be stretched and shaped over irregular surfaces, even those of multiple curvatures. Then when bonded into place, the sheet will harden again. This can be one operation. The thus hardened substrate material will crack when a crack or rupture occurs in the metal but will not be subject to fatigue, nor like wires have the tendency to bridge over the cracks. Also, the material unlike that of the Crites patent is not sensitive to low temperatures, but will function as a crack sensor where that material is unable to function. It is obvious that other plastic materials can be used to make the flowable conducting substance and substrate. Also it is recognized that these materials can be softened when used as a substrate to conform to irregular surface or multiple curvatures and can be hardened thereafter.

EXAMPLE 2

In another example, similar to Example 1, an acrylic powder was mixed with the conducting particulate material, graphite and softened with the acrylic monomer, and a catalytic agent such as benzyl peroxide was added to make the flowable conductive line-forming substance.

The base or substrate layer used was a similar plastic layer and the conductive lines were formed thereon by the syringe method described above. The plastic substrate layer was first softened by methylene chloride. After application of the conductive lines, the substrate layer was softened in a similar manner and applied to the structure to be protected.

EXAMPLE 3

A polyester or an epoxy powder was used as in Example 1 with a suitable catalyst. Various catalysts such as tetraethylamine, were used.

EXAMPLE 4

The line-producing substance used in this example included a polystyrene powder to which was added a common polystyrene solvent. The substrate used was a thin sheet of polystyrene.

After the pattern was formed in the substrate sheet, the sheet was softened and rebonded to the structure to be protected.

EXAMPLE 5

A cellulose acetate sheet was used as the substrate. The electrical conducting lines were then applied to the sheet. The sheet was then formed and bonded to the surface to be protected.

Other examples of the system of this invention are:

EXAMPLE 6

Step 1. A die mould was prepared by cutting a thread on the polished surface of an aluminum bar 3-inch in diameter and 6-inches long. The threads can be 50 per inch. The depth of the thread 0.004 inch and the width of the cut 0.004 inch. A very thin coating of parting compound was applied.

Step 2. A conducting viscous liquid mixture of commercial cellulose acetate cement and super conducting carbon, using 2 parts by weight of carbon to 3 parts by weight of cement was prepared. Then the grooves in the aluminum die were filled with the mixture, removing all excess.

Step 4. A very thin coating of cement (cellulose acetate) to one surface of a 2 to 3 mil sheet of cellulose acetate film was applied. The sheet of a size sufficient to wrap around the die was filled with the conducting cement. It was tightly wrapped around the die and allowed to dry thoroughly. After drying, it was removed and checked for electrical continuity. The sheet was then ready to apply to a structure. An insulating protective coating was applied after making the electrical connections. If the sheet is to be applied to an irregular or doubly curved surface it would be necessary to first soften the sheet by soaking in an acetone-water solution. The pliable sheet could then be conformed to the surface and cemented into place. The sheet material could then be baked.

EXAMPLE 7

Step 1. The die was used as directed in Example 6 and the grooves were filled with a mixture of copper dust or fine powdered copper and the cellulose acetate cement in a ratio of 2 to 1.

Step 2. All the remaining steps as in Example 2 were then followed.

EXAMPLE 8

Step 1. Step one in Example 6 was followed. In step 2, commercial conducting epoxy, using silver as the conducting material was substituted.

Step 2. The grooves in the die mould were filled with the conducting silver epoxy.

Step 3. The die mould was coated evenly with a clear epoxy coating. Then when the coating was set up, but not completely hard, a cut was made through the epoxy lengthwise and the epoxy was peeled off. (Lightly oiling the fingers allowed this to be done). Then while the coating was still flexible or pliable, it was cemented in place. Connections, using silver mixture as solder, were then made.

It will be apparent from the above description that this invention provides a detecting system for detecting defects in structures which comprises an assembly that can be produced at low cost and can be easily applied to the surface of a structure to be monitored for cracks or rupturing. The assembly consists basically of an insulating layer which carries lines of conducting material formed of small particles in electrical contact. The layer hardens or is hardened, after application to the surface to be protected, so that it will crack or rupture if a crack or rupture occurs in the surface, and thereby separate the particles in the conducting line or lines adjacent the crack or rupture, which may actuate an indicating circuit. The layer may be elastomeric at the time of application or may be brittle and be cemented to the surface.

Having thus described the invention what is claimed is:

1. A crack or rupture detecting system comprising an electrically-insulated substrate layer of material which is applied while elastomeric to an object to be monitored so it will conform thereto but hardens and is capable of cracking or rupturing, said substrate carrying conductive lines formed by small conductive particles in electrical contact which will separate upon the occurrence of a crack or rupture in the substrate, indicating an adjacent crack or rupture in the object and an indicating system connected in circuit with said conductive lines.

2. A system according to claim 1 in which the substrate layer with the conducting lines thereon is covered by an insulating layer.

3. A system according to claim 1 applied to the object to be monitored in which the substrate is adhered to a surface of the object and is caused to conform to the contour thereof.

4. A system according to claim 3 in which the substrate is cemented to the object.

5. A system according to claim 3 in which the conducting lines are connected in an electric indicating circuit.

6. A system according to claim 5 in which the particles range in size from 1 to 100 microns.

7. A system according to claim 6 in which the particles are selected from the group consisting of carbon particles and metal particles.

8. The method of monitoring an object for cracks or ruptures which comprises applying an elastomeric insulating substrate to a surface of the object so it will conform thereto but will then harden so it can subsequently crack or rupture, the substrate being provided with conductive lines formed of conductive particles in electrical contact which will separate upon the occurence of a crack or rupture in the substrate to indicate a crack or rupture in the surface of the object, and connecting an indicating system in circuit with said conducting lines.

9. The method of claim 8 in which the substrate is cemented to the surface.

10. The method of claim 8 in which the particles applied to the substrate layer are applied as a viscous substance consisting of a liquid carrier and the particles, which subsequently dries or sets.

11. The method of claim 10 in which the particles are selected from the group consisting of carbon particles and metallic particles ranging in size from 1 to 100 microns.

12. The method of claim 11 in which the particles used are in amounts of 15 to 100 parts of carbon to 100 parts of liquid carrier by weight or 2 to 3 parts of metal particles to 1 part of liquid carrier.

* * * * *